(12) United States Patent
Fishbein et al.

(10) Patent No.: US 6,535,754 B2
(45) Date of Patent: Mar. 18, 2003

(54) LEVER COIL SENSOR FOR RESPIRATORY AND CARDIAC MOTION

(75) Inventors: Kenneth W. Fishbein, Cockeysville, MD (US); Richard G. S. Spencer, Baltimore, MD (US); Patrick McConville, Perry Hall, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 22 days.

(21) Appl. No.: 09/822,881

(22) Filed: Mar. 30, 2001

(65) Prior Publication Data

US 2002/0183611 A1 Dec. 5, 2002

(51) Int. Cl.[7] .................................................. A61B 5/05
(52) U.S. Cl. ...................... 600/422; 600/411; 600/413; 600/414
(58) Field of Search ................................ 600/411, 422, 600/534, 413, 428, 535, 536; 324/307, 309, 318, 320

(56) References Cited

U.S. PATENT DOCUMENTS

| | | |
|---|---|---|
| 5,035,244 A | 7/1991 | Stokar |
| 5,038,785 A | 8/1991 | Blakeley et al. |
| 5,427,101 A | 6/1995 | Sachs et al. |
| 5,729,140 A | 3/1998 | Kruger et al. |
| 6,073,041 A | 6/2000 | Hu et al. |
| 6,088,611 A | 7/2000 | Lauterbur et al. |

OTHER PUBLICATIONS

Fishbein et al., "The lever–coil: a simple, inexpensive sensor for respiratory and cardiac motion in MRI experiments," *Magnetic Resonance Imaging*, vol. 19, pp. 881–889 (2001).

Axel, L. et al., "Respiratory Effects in Two–Dimensional Fourier Transform MR Imaging[1]", *Radiology*, vol. 160, No. 3, pp. 795–801 (1986).

Babchenko, A. et al., "Fiber Optic Sensor for the Measurement of Respiratory Chest Circumference Changes", *Journal of Biomedical Optics*, vol. 4, No. 2, pp. 224–229 (Apr. 1999).

(List continued on next page.)

*Primary Examiner*—Marvin M. Lateef
*Assistant Examiner*—Devaang Shah
(74) *Attorney, Agent, or Firm*—Merchant & Gould P.C.

(57) ABSTRACT

The invention includes a device for detection of respiratory motion of a subject during acquisition of an magnetic resonance image that includes a lever having a proximal and a distal end, a counterweight on the proximal end of the lever, a fulcrum, a pickup coil attached to the distal end of the lever, and a MRI machine that has a radio frequency resonator, a gradient coil, and a magnetic field, wherein the lever, fulcrum, counterweight, and pickup coil are positioned so that the lever moves as the subject breathes, the pickup coil is also positioned so that it does not cause artifacts in the MRI image, and the device as a whole generates an electrical signal that can be used to detect and monitor the respiratory motion of the subject. The invention also includes a device for respiratory gating of a magnetic resonance imaging experiment including a lever having a proximal and a distal end, a counterweight on the proximal end of the lever, a fulcrum, a pickup coil attached to the distal end of the lever, and a MRI machine that has a radio frequency resonator, a gradient coil, and a magnetic field, wherein the lever, fulcrum, counterweight, and pickup coil are positioned so that the lever moves as the subject breathes, the pickup coil is also positioned so that it does not cause artifacts in the MRI image, and the device as a whole generates an electrical signal that can be used to detect and monitor the respiratory motion of the subject and the threshold detector is used to trigger the acquisition of the individual scans of the magnetic resonance image.

24 Claims, 11 Drawing Sheets

OTHER PUBLICATIONS

Bailes, D. R. et al., "Respiratory Ordered Phase Encoding (ROPE): A Method for Reducing Respiratory Motion Artefacts in MR Imaging", *Journal of Computer Assisted Tomography,* vol. 9, No. 4, pp. 835–838 (Jul./Aug. 1985).

Brauer, M. et al., "*In Vivo* Proton Nuclear Magnatic Resonance Imaging and Spectroscopy Studies of Halocarbon–Induced Liver Damage", *Magnetic Resonance in Medicine,* vol. 9, pp. 229–239 (1989).

Buikman, D. et al., "The RF Coil as a Sensative Motion Detedor for Magnetic Resonance Imaging", *Magnetic Resonance Imaging,* vol. 6, No. 3, pp. 281–289 (1988).

Burdett, N. G. et al., "A Simple Device for Respiratory Gating for the MRI of Laboratory Animals", *Magnetic Resonance Imaging,* vol. 11, pp. 897–901 (1993).

Cockman, M.D. et al., "Motion Suppression Improves Quantification of Rat Liver Volume in Vivo by Magnetic Resonance Imaging", *MRM,* vol. 30, pp. 355–360 (1993).

Ehman, R. et al., "Magnetic Resonance Imaging with Respiratory Gating: Techniques and Advantages", *AJR* vol. 143, pp. 1175–1182 (Dec. 1984).

Ehman, R., et al., "Adaptive Technique for High–Definition MR Imaging of Moving Structures", *Radiology,* vol. 173, No. 1, pp. 255–263 (Oct. 1989).

Felblinger, J. et al., "Amplitude Demodulation of the electrocardiogram Signal (ECG) for Respiration Monitoring and Compensation during MR Examinations", *MRM,* vol. 38, pp. 129–136 (1997).

Fichtner, K–P. et al., "*In Vivo* $^1$H–NMR Microimaging with Respiratory Triggering for Monitoring Adoptive Immunotherapy of Metastatic Mouse Lymphoma", *MRM,* vol. 38, pp. 440–455 (1997).

Fishbein K., et al., "The lever–coil: a simple, inexpensive sensor for respiratory and cardiac motion in MRI experiments", *Magnetic Resonance Imaging,* vol. 19, pp. 1–9 (2001).

Hashimoto, Y. et al., "Cardiogenic ballistograms of chicken eggs: comparison of measurements", *Medical & Biological Engineering & Computing,* vol. 29, No. 4, pp. 393–397 (Jul. 1991).

Henneberg, S. et al., "Remote Auscultatory Patient Monitoring During Magnetic Resonance Imaging", *Journal of Clinical Monitoring,* vol. 8, No. 1, pp. 37–43 (Jan. 1992).

Jansen, B. et al., "Monitoring of the Ballistocardiogram with the Static Charge Sensitive Bed", *IEEE Transactions on Biomedical Engineering,* vol. 38, No. 8, pp. 748–751 (Aug. 1991).

Johansson, A. et al., "Monitoring of Heart and Respiratory Rates in Newborn Infants Using a New Photoplethysmographic Technique", *Journal of Clinical Monitoring and Computing,* vol. 15, Nos. 7–8, pp. 461–467 (Dec. 1999).

Keller, P. et al., "Gradient Moment Nulling through the Nth Moment. Application of Binomial Expansion Coefficients to Gradient Amplitudes", *Journal of Magnetic Resonance,* vol. 78, pp. 145–149 (1988).

Lemieux, S. et al., "An Infrared Device for Monitoring the Respiration of Small Rodents During Magnetic Resonance Imaging", *JMRI,* vol. 6, pp. 561–564 (May/Jun. 1996).

Lindberg, L.–G et al., "Monitoring of respiratory and heart rates using a fibre–optic sensor", *Medical & Biological Engineering & Computing,* vol. 30, pp. 533–537 (Sep. 1992).

McKibben, C. et al., "A Piezoelectric Respiratory Monitor for *in Vivo* NMR", *Magnetic Resonance in Medicine,* vol. 27, pp. 338–342 (1992).

Minard, K. et al., "A compact respiratory–Triggering Device for Routine Microimaging of Laboratory Mice", *JMRI,* vol. 8, pp. 1343–1348 (Nov./Dec. 1998).

Nakajima, K. et al., "Monitoring of heart and respiratory rates by photoplethysmography using a digital filtering technique", *Med. Eng. Phys.,* vol. 18, No. 5, pp. 365–372 (Jul. 1996).

Ono, H. et al., "Ballistocardiogram of avian eggs determined by an electromagnetic induction coil", *Med. Biol. Eng. Comput.,* vol. 35, pp. 431–435 (Jul. 1997).

Polo, O. et al., "Respiratory variation of the ballistrocardiogram during increased respiratory load and voluntary central apnoea", *Eur. Respir. J.,* vol. 5, No. 2, pp. 257–262 (1992).

Rubin, J. et al., "Doppler US Gating of Cardiac MR Imaging", *Academic Radiology,* vol. 7, No. 12, pp. 1116–1122 (Dec. 2000).

Runge, V. et al., "Respiratory Gating in Magnetic Resonance Imaging at 0.5 Tesla", *Radiology,* vol. 151, pp. 521–523 (1984).

Schmidt, P. et al., "Physiological Monitoring during NMR Measurements of Animals", *Journal of Magnetic Resonance,* vol. 54, pp. 480–485 (1983).

Slawson, S. E. et al., "Cardiac MRI of the Normal and Hypertrophied Mouse Heart", *MRM,* vol. 39, pp. 980–987 (1998).

Van Bruggen, N. et al., "Indentification of Tumor Hemorrhage in an Animal Model Using Spin Echoes and Gradient Echoes", *Magnetic Resonance in Medicine,* vol. 15, pp. 121–127 (1990).

Whalen, M. et al., "Controlled Ventilation During NMR Spectroscopic Studies: Hemodynamic and Biochemical Consequences", *Magnetic Resonance Imaging,* vol. 9, No. 2, pp. 229–234 (1991).

Wilson, S. et al., "Respiratory Triggered Imaging with an Optical Displacement Sensor", *Magnetic Resonance Imaging,* vol. 11, No. 7, pp. 1027–1032 (1993).

Fishbein, K. et al., Presentation given at proceedings of the International Society for Magnetic Resonance in Medicine(2000).

LEVER COIL SENSOR FOR RESPIRATORY AND CARDIAC MOTION

FIELD OF THE INVENTION

The invention relates generally to a device that detects respiratory and cardiac motion in mammals. More specifically, the invention relates to a device which when mechanically coupled to an animal in a magnetic resonance imaging ("MRI") scanner detects respiratory and cardiac activity through a pickup coil but does not create artifacts in the MRI image.

BACKGROUND OF THE INVENTION

Respiratory and cardiac motion can cause severe blurring in magnetic resonance imaging ("MRI") studies of the thoracic or abdominal region when the total duration of the experiment is not short compared to the respiratory and/or cardiac period. For such experiments, a variety of methods exist to reduce the effects of respiratory motion on the resulting images. Such methods can be broadly classified into four different types, modifying the subject of the image, nuclear magnetic resonance ("NMR") based methods, direct non-NMR based methods, and indirect non-NMR based methods.

One method of minimizing motion that causes blurring is to modify the patient in one way or another. For example, the patient can be asked to hold their breath. Although this can minimize respiratory motion and eliminate blurring, it is not applicable to animal subjects and cannot be used with some patients with respiratory or other illnesses. Patients can also be intubated, or mechanically ventilated. This permits exact synchronization of MRI data acquisition to the respiratory cycle. However, this may induce significant reductions in cardiac output and liver blood flow compared to free breathing, and is an invasive procedure that is often not desirable for a relatively simple MRI procedure.

Certain NMR based methods also exist that can minimize blurring of MRI images due to motion of the subject. One such method is called the navigator echo technique. The navigator echo technique is accomplished by acquiring a one-dimensional profile along the motion direction. This allows the respiratory phase to be measured at any given time. Once the respiratory phase has been determined, it can be used to produce artifact-free images, but this method is applicable only for simple motion that has a period that is long compared to the time required to acquire one phase-encoded step. Gradient moment nulling is another NMR based method for limiting or eliminating artifacts from motion. Gradient moment nulling eliminates the net evolution of nuclear spins moving in the magnetic field gradient by varying the amplitude and/or duration of the gradient. Gradient moment nulling, although applicable in human experiments, is an insufficient technique for small animal imaging.

There are also a number of direct non-NMR methods that are useful to eliminate blurring caused by motion. Optical sensors can detect chest motion when placed on the chest of the subject. Motion can be detected for example by placing the fiber so that the motion causes the fiber to flex which interrupts the light propagation through the fiber. Optical fibers can also detect motion when the motion causes a variation in the distance of the chest to an infrared emitter/detector. Both methods of using optical fibers detect respiratory motion through monitoring of the absolute chest position. Such techniques are advantageous in that they do not require electrical leads inside the probe or magnet, but are limited because of the need for very careful placement and maintenance of the fiber on or near a specific part of the subject's chest. Another method of direct non-NMR detection of respiratory motion is through the use of a pickup coil. Pickup coils generate a signal through electromagnetic induction in a wire loop placed on the subject's chest within a magnetic field. Pickup coils are inexpensive to build and easy to use, but require wire leads to be placed within the radio frequency ("RF") coil and gradients. These leads can introduce RF interference artifacts' pose a potential hazard of burns due to mutual inductance within the RF and/or gradients, and are subject to artifacts in the respiratory signal during scanning.

There are also indirect non-NMR based methods that can be used to minimize. artifacts caused by motion. Many of these methods are based on the effects (on the subject and the immediate area surrounding the subject) of breathing. One such method utilizes a pressure detector on the chest of the subject with a pressure sensor outside the RF coil. Examples of such detectors are strain gauges, air bellows, or balloons. Although the theory behind these types of sensors is straightforward, they are quite sensitive to temperature variations, drifting baselines, and leakage. Also, they are generally not amenable to use on small animals. The temperature and carbon dioxide content of exhaled air can also be used to monitor respiration, but the response is too slow for use in small, rapidly breathing animals. Another method that takes advantage of the effects of respiration is plethysmography. A plethysmograph utilizes an airtight chamber housing the subject, and uses a remote airflow sensor to detect motion of the subject. Although this type of sensor is quite useful in animals, it is quite expensive, complex and limits access to the animal. It is also highly unlikely, because of the sealed chamber, that such a method would be used with human subjects. Photoplethysmography, can also be used. Photoplethysmography detects respiratory and cardiac variations in superficial blood flow by infrared light scattering, but is again not amenable to imaging of small animals.

There are also methods that use certain characteristics of the MRI imaging process itself. For example, respiratory ordered phase encoding (ROPE) which is generally used along with a technique (either NMR or non-NMR based) to measure respiratory motion, can be used to generate artifact-free images, but requires specialized hardware and software, not generally available on animal imaging systems, to reconstruct the data. The data is acquired and processed with a mathematical algorithm that uses the respiratory phase signal to correct for the simple motion caused by respiration. Another method is the measurement of probe Q modulation, which allows for the detection of both respiratory and cardiac motion but requires special spectrometer hardware and can be prone to errors due to non-respiratory motion of the animal.

A number of patents have been directed towards methods of reducing image blurring due to motion. For example, U.S. Pat. No. 5,035,244 (Stokar), basically discloses an improvement on ROPE. It is a method that measures respiratory displacement data and uses that data to set the phase encoding gradient in order to minimize artifacts caused by motion. The important aspect of the invention is the mathematical algorithm that is utilized to select the phase encoded gradient strengths based on the respiratory displacement data. The disadvantages of this method are first, that a standard sensor, which has significant drawbacks, is necessary to obtain the respiratory displacement data, and second that it does not remedy the effects of cardiac motion.

U.S. Pat. No. 5,038,785 (Blakely, et al.) discloses a method of using electrodes to monitor the cardiac cycle and an expansion belt to monitor the respiratory cycle of a patient being imaged. During a MRI scan, noise wave forms or spikes are superimposed on the cardiac cycle signal. A noise spike detector detects spikes. Specifically, a comparator compares each wave form received from the electrodes with properties of a cardiac signal, such as the slope. When the comparator determines that a noise wave form is being received, it gates a track and hold circuit. The track and hold circuit passes the received signal except when gated by the comparator. When gated by the comparator, the track and hold circuit continues to, supply the same output amplitude as in the beginning of the gating period. A filter then smoothes the plateaus in the cardiac signal formed as the noise signal waveforms are removed.

U.S. Pat. No. 5,427,101 (Sachs, et al.) discloses a method of reducing motion artifacts in MRI images through use of an algorithm. The method first acquires an initial set of data frames that includes a mechanism for indicating a relative position of each frame. The positional markers in these data frames are then evaluated and those that are deemed positionally worse are reacquired.

U.S. Pat. No. 5,729,140 (Kruger, et al.) teaches to a method for removing artifacts from NMR images by acquiring two data sets from which a desired image can be reconstructed, calculating the correlation between the two data sets to produce a correlation array, and producing a corrected image from the correlation array.

U.S. Pat. No. 6,073,041 (Hu, et al.) discloses a method for the removal of signal fluctuation due to physiological factors such as respiration and cardiac pulsations. The technique comprises simultaneous measurement of physiological motion during MRI data acquisition. Then in post processing steps, imaging data are retrospectively ordered into unit physiological cycles, after which the physiological effects are estimated and removed from the MRI data.

U.S. Pat. No. 6,088,611 (Lauterbur, et al.) teaches to a method for obtaining high-resolution snapshot images of moving objects in MRI applications through the elimination of ghosting and other image artifacts. The method works by estimating motion frequency data, estimating the amplitude data for the motion frequency data, interpolating the motion frequency data and the amplitude data to generate snap-shot data frames, and generating snapshot images of each snapshot data frame.

Commercially available sensors, as well as the methods discussed above are either unreliable, unworkable in certain situations, or are too expensive. Therefore, there remains a need for a method of simultaneously detecting cardiac and respiratory motion that is reliable, amenable to different kinds of subjects, and is relatively inexpensive.

SUMMARY OF THE INVENTION

The device of the invention uses a small electromagnetic pickup coil coupled to a mechanical lever to sense the respiratory and cardiac motion of a subject in a MRI scanner. It generates an electrical signal that is proportional to the velocity of motion. This signal can be used to synchronize the MRI scanner to prevent blurring induced by motion during the MRI scan. Unlike earlier pickup coil sensors, the device of the invention uses a mechanical linkage to keep the pickup coil outside the scanner's RF and gradient coils, thereby eliminating artifacts in the sensor signal and MR images caused by mutual inductance.

The device of the invention is unique in that it can simultaneously detect both cardiac and respiratory motion from a mammal in a MRI scanner without any electrical leads inside the magnet. This allows artifact free monitoring of respiratory and cardiac motion by use of an intrinsically safe device. The device generates a strong signal even when the actual movement of the device upon respiration is small, therefore, it is ideally suited for small animal experiments. Because it is not necessary to have precise placement of the device, it can be used with the subject in any position, including prone, supine, etc. It can also be inserted and removed from the magnet without repositioning the subject; allowing for quick access to the subject for visual inspection, injections, etc.

The signal that the device generates is proportional to the velocity of the motion, therefore no motion implies zero signal; this allows for a simple threshold detector to be used to trigger image acquisition based on the signal of the device since DC offsets are absent. The device simultaneously and directly detects motion due to both cardiac and respiratory cycles, therefore it would not be necessary to have electrocardiogram ("ECG") leads on the patient.

DETAILED DESCRIPTION OF THE PREFERRED EMBODIMENTS

Figure 1:
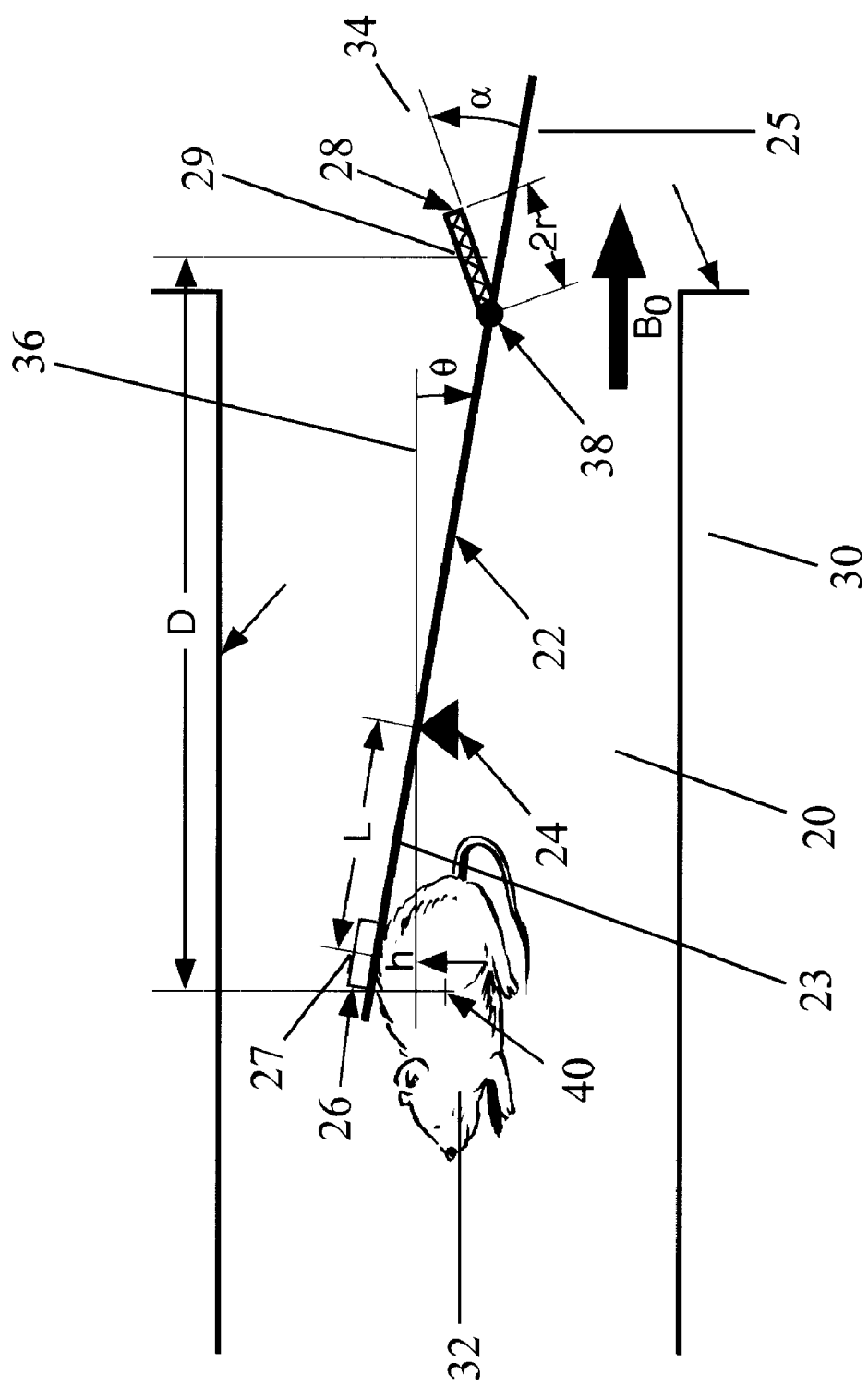
FIG. 1 is a schematic of a device in accordance with the invention configured for use on a subject with a magnet bore representing the whole of a MRI machine.

FIG. 1 depicts a simple schematic of a device 20 in accordance with one aspect of the invention configured for use on a subject 32 with a magnet bore 30 representing the whole of a MRI machine. A device 20 in accordance with the invention comprises a lever 22, a fulcrum 24, a counterweight 26, and a pickup coil 28.

The lever 22 functions, in concert with filcrum 24, to move lever 22 relative to the magnet z axis 36 when the subject 32 moves. Typically the movement of lever 22 is into the sagittal (Y-Z) plane, but can be in any plane. This flexibility allows the lever 22 to be more easily placed on the subject 32. The magnet z axis 36 is defined by the z axis of magnet bore 30. Lever 22 has a proximal end 23 and a distal end 25. Generally lever 22 can be made of any material that is rigid, nonconductive and nonmagnetic. For example, lever 22 can comprise wood, plastic, fiberglass, carbon fiber, ceramic, or the like. Preferably, lever 22 comprises wood, or a soft plastic to minimize intrinsic vibrations within lever 22.

Fulcrum 24 functions, in concert with lever 22, to allow lever 22 to move relative to the magnet z axis 36 when subject 32 moves. Fulcrum 24 basically acts as a fulcrum point for lever 22. Generally fulcrum 24 can comprise any structure that allows lever 22 to move relative to the magnet z axis 36. For example, fulcrum 24 may be a pyramid with lever 22 balanced on it, or fulcrum 24 may be a hollow cylinder that houses lever 22 and can be secured to a non-moveable frame. Preferably, fulcrum 24 is a hollow cylinder that houses lever 22, and allows it to move relative to the magnet z axis 36. Fulcrum 24 can comprise any material that is rigid, nonmagnetic material. For example, fulcrum 24 may comprise plastic, nonmagnetic stainless steel, brass, titanium, bronze, ceramic or the like. Preferably, fulcrum 24 comprises brass.

When device 20 is configured for use on a subject 32, the lever 22 and the magnet z axis 36 define an angle $\theta$ called the nominal fulcrum angle. $\theta$ is the angle formed by lever 22 and magnet z axis 36 at the end of subject 32 expiration, when the chest isn't moving. The range of $\theta$ depends on the magnet bore 30 and the height of the subject in the plane in which the lever 22 moves. Theoretically, a larger $\theta$ will produce a larger signal, but practically, $\theta$ is limited based on the inner diameter of the magnet, the gradient coil and the RF coil and the distance from the front or back of the magnet (depending on the configuration of the device 20 with the MRI machine) to the magnet center 40.

Counterweight 26 functions to keep lever 22 on subject 32. Counterweight 26 has a center 27. The weight of counterweight 26 depends both on the weight of pickup coil 28, the distance along the lever from the center 27 of counterweight 26 to the fulcrum 24 (called the counterweight to fulcrum distance L), and the distance from the pickup coil 28 to the fulcrum 24. Preferably, counterweight 26 will be of a shape that allows it to be easily placed on a subject 32 and maintains counterweight 26 on the subject 32 even with movement. Counterweight 26 can comprise nonmagnetic and nonconductive material. Preferably counterweight 26 is made of a material that is sterilizable or is inexpensive enough to manufacture that it is disposable. For example, wood, plastic, ceramic, glass, or the like. Preferably, counterweight 26 will comprise a material that will not be detrimental to the subject 32. Preferably, counterweight 26 comprises Teflon™ because it does not produce a background signal in a proton MRI scan.

Pickup coil 28, located outside the sensitive region of the RF resonator coil and gradient coil but within the magnetic field $B_0$, functions to generate an electrical signal when the lever 22 moves relative to the magnet z axis 36. The electrical signal is generated by electromagnetic induction. The magnitude of the electrical signal produced by the pickup coil 28 is determined in part by the size and configuration of pickup coil 28. Generally, the pickup coil 28 is made by winding a wire into a spiral. The more turns there are in the configuration of the pickup coil 28, the greater the signal that will be produced when it is in magnetic field $B_0$. Preferably, pickup coil 28 is wound as a spiral in a single plane. Theoretically, pickup coil 28 is characterized by the radius r of the circular area of a single coil. However, a spiral coil can also be characterized by its radius, r, without introducing substantial error. Pickup coil 28 can comprise any nonmagnetic conductive material. For example, copper, silver, aluminum or the like. Preferably, pickup coil 28 comprises copper.

Pickup coil 28 is attached to lever 22 at coil mounting 38. Coil mounting 38 can afford either a stationary attachment between pickup coil 28 and lever 22 or can allow pickup coil plane 34 to be varied. Pickup coil plane 34 and lever 22 define an angle $\alpha$ called the coil angle. Coil mounting 38 can comprise any material and configuration that allows for either stationary or adjustable connection of pickup coil 28 to lever 22. For example, coil mounting 38 can comprise plastic, such as acrylic plastic, or the like. Preferably, coil mounting 38 comprises acrylic plastic and does allow for movement of pickup coil 28 and thereby adjustment of the coil angle $\alpha$. The coil angle $\alpha$ can range from about 0° to 90°. It is preferred that coil angle $\alpha x$ is approximately equal to the nominal fulcrum angle $\theta$.

Magnet bore 30 is a simplified representation of the whole of the MRI machine. A device 20 in accordance with the invention can be used with any MRI machine that has a configuration, or can be modified to have a configuration that allows the device 20 to be configured correctly inside and outside of the machine. Because of the relatively small size of the device 20 and its limited motion while functioning, the device 20 should be able to be configured with most open or horizontal MRI machines. A device 20 of the invention would be able to be used with a vertical machine if the lack of effect of gravity were remedied through use of a spring or the like. It should also be noted that the terms radio frequency resonator, RF resonator, RF coils, or combinations thereof encompass standard radio frequency resonator coils as well as localized surface coils and phased-array coils as well.

Examples of MRI machines that can be used with a device 20 of the invention include but are not limited to, a Biospec MRI scanner equipped with 20 cm shielded gradients and 15 cm proton resonator by Bruker Medizintechnik GMbH (Ettlingen, Germnany); GE Signa scanners (GE Medical Systems, Waukesha, Wis.); Hitachi MRI scanners (Hitachi Medical Systems, Twinsburg, Ohio), Marconi MRI scanners (Marconi Medical Systems, Cleveland, Ohio), Phillips MRI scanners (Phillips Medical Systems, Best, Netherlands), Siemens Magnetom machines (Siemens Medical Systems, Erlangen, Germany); Toshiba MRI scanners (Toshiba Medical Systems, Tustin, Calif.); and Varian MRI machines (Varian, Palo Alto, Calif.). Magnet bore 30 creates a magnetic field $B_0$ that has a certain magnitude. The magnetic field $B_0$ defines the magnet z axis 36.

Subject 32 is the mammal to be imaged by the MRI machine. Subject 32 can be any animal, including but not limited to, humans, monkeys, dogs, mice, and rats. The subject 32 need only have lungs and a heart if both respiratory and cardiac motion are to be monitored. Different subjects 32, often dictate the use of different MRI machines because of the size constraints of the MRI machine. Subject 32 is generally positioned at the center of the magnetic field 40.

The distance from the center of the magnetic field 40 to the center 29 of the pickup coil 28, defined by the radius of the circular area r, is called the subject to pickup coil distance D. The subject to pickup coil distance D is dictated in part by the specific MRI machine utilized with the device 20. With any particular MRI machine, the subject to pickup coil distance D must be large enough that mutual inductance between the pickup coil 28 and the RF resonator and gradients are minimized, while at the same time small enough that there is an electrical signal generated in the pickup coil 28. The placement of the pickup coil 28 in the RF coils can be characterized by using the "sensitive region" of the RF coil. The sensitive region of the RF coil generally corresponds with the region in the magnetic resonance imaging machine where nuclear spins can be detected if they are present in that area. The region where nuclear spins can be detected if they are present in that area usually corresponds with the homogeneous region of the magnetic field, $B_0$. One placement of the pickup coil 28 that generally allows all of the constraints to be satisfied is to place the pickup coil 28 just outside the gradient and RF coils.

The center of the magnetic field 40 also defines the counterweight height h, which is the distance in the vertical direction from the center of the magnetic field 40 to the subject's 32 surface.

The enumerated components given above are configured, for example as in FIG. 1. Generally, the configuration of the device is dictated in part by the MRI machine used and by the method of operation of the device 20 as discussed below.

Referring to FIG. 1, and the accompanying discussion above, the method by which a device 20 of the invention works to detect respiratory and/or cardiac motion will now be explained. Motion of the subject's 32 chest causes a lever 22 to fulcrum up and down on fulcrum 24, thereby moving pickup coil 28, which is positioned outside the sensitive region of the RF resonator and far enough from the center of the magnetic field to minimize coupling with the RF and gradient coils. The induced electromotive force ε in the pickup coil 28 is given by Faraday's law; shown in equation 1:

$$\varepsilon = -\frac{d\phi}{dt} \quad (1)$$

where φ is the magnetic flux through the pickup coil 28 at time t. If the pickup coil 28 is planar and has a single turn, the flux through the pickup coil 28 is given by equation 2. At any time the flux through the pickup coil is the product of the incident magnetic field, the area of the coil, and the sine of the coil angle with respect to the magnetic field. In equation 2, B is the magnitude of the static magnetic field $B_0$ at the location of the pickup coil 28 and r is the radius of the pickup coil 28.

$$\phi = B\pi r^2 \sin(\alpha - \theta) \quad (2)$$

It should be noted at this time that the theory of operation of the device 20 is based on a planar, single loop pickup coil 28 with radius r. However, generally, the pickup coil 28 will not be a planar, single loop. Changing the pickup coil 28 from a planar, single loop will not alter the functioning of device 20, or the relevant calculations. The only effect that a multiple turn pickup coil 28 will have on the device 20 is to amplify the signal received. Therefore, for ease of calculation, it will be assumed that pickup coil 28 is a planar, single coil of wire.

Equation 2 assumes that the field generated by the magnet is homogeneous over the volume of the pickup coil 28 and that this field is oriented along the magnet axis. Clearly, this approximation is valid only when the pickup coil 28 is located a relatively short distance from the center of the magnetic field 40. Since the tilt angle of the pickup coil 28 relative to the lever, the coil angle α, does not vary with the motion of the lever, the time dependence of the flux is completely due to the variation of θ, the nominal lever angle, the angle between the lever 22 and the magnet z axis 36, with the motion of the subject 32.

Based on FIG. 1, sin θ=h/L, so the flux is given by equation 3:

$$\frac{d\phi}{dt} = -\frac{B\pi r^2}{L}\frac{\cos(\alpha-\theta)}{\cos\theta}\frac{dh}{dt} \quad (3)$$

If equation 3 is combined with equation 1, the result is given as equation 4 below:

$$\varepsilon = \frac{B\pi r^2}{L}(\cos\alpha + \tan\theta\sin\alpha)\frac{dh}{dt} \quad (4)$$

Thus, we predict that the maximum induced current occurs when the counterweight to fulcrum distance L is minimized, the nominal fulcrum angle θ is maximized and the coil angle α is equal to θ. This last condition is equivalent to placing the pickup coil plane 34 parallel to the $B_0$ field with the lever 22 at its nominal fulcrum angle θ. When the pickup coil plane 34 is close to parallel to $B_0$, α−θ is small, the dependence of the induced electromotive force, ε, on the coil angle α is very weak. This implies that the coil angle α does not need to be carefully optimized to give a strong electrical signal from the device 20. Note that if the coil plane 34 were parallel rather than perpendicular to the plane of the paper in FIG. 1, the incident flux φ on the coil would be zero and there would be no induced signal from the device. Also, note that while minimizing the counterweight to fulcrum distance L increases the magnitude of the induced voltage, this voltage has no explicit dependence on how far the pickup coil 28 is placed form the magnet center 40. Thus, the pickup coil 28 may be moved as far away as needed to avoid coupling to the RF resonator and gradients without a loss in induced signal as long as $B_0$ remains strong. Of course, in a real magnet, $B_0$ will decrease and become increasingly inhomogeneous with increasing distance from the magnet center 40, so the optimum coil to fulcrum distance will vary depending on magnet, gradient coil, and RF resonator dimensions.

WORKING EXAMPLES

The following examples provide a nonlimiting illustration of the application and benefits of the invention.

Example 1

Figure 2:
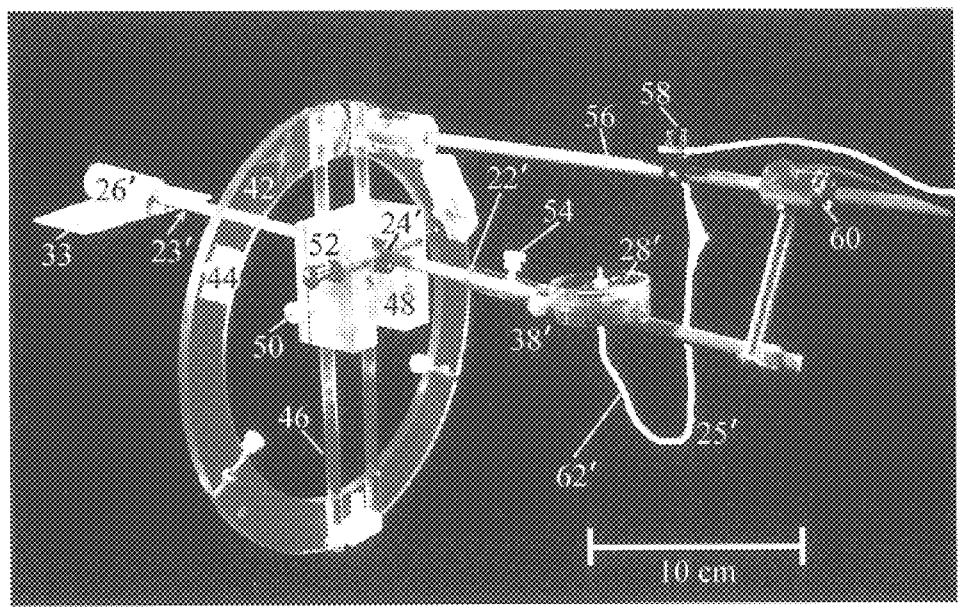
FIG. 2 illustrates one embodiment of a device in accordance with the invention.

Example 1 represents a specific device made in accordance with one aspect of the invention. The device is depicted in FIG. 2, and reference will be made to FIG. 2 when discussing the construction of the device. The device depicted in FIG. 2 is a specific example of a device that is consistent with the device depicted in FIG. 1, and like numbers, with the exception of a dash ('), will be used to refer to like structures.

The device 20' can be built using common, inexpensive materials. The lever 22' depicted in FIG. 2 is a simple wooden dowel, 61 cm (2 ft) in length, and 0.64 cm (¼ inch) in diameter.

The fulcrum 24' is made of brass and rotates about needle bearings 52 made of 321 stainless steel. Fulcrum 24' is 2.54 cm (1 inch) in length and has an outer diameter of 1.27 cm (½ inch). Although it cannot be seen in FIG. 2, fulcrum 24' houses a screw on its bottom face. This screw functions to allow for adjustment of the counterweight to fulcrum distance, L. This screw in this embodiment is a 10–32×½" nylon screw.

Counterweight 26 is made of Teflon™ in this embodiment. Counterweight 26' is a 3.8 cm (1.5 inch) long and 1.90 cm (¾ inch) in diameter cylinder that fits on the end of lever 22'. An optional paddle 33 can be attached to counterweight 26' to minimize slipping of counterweight 26' off of the subject 32. Paddle 33 is made from a sheet 1/16 inch (about 0.16 cm) thick of Teflon™. The pickup coil 28' is made of 0.25 mm copper wire. A 3.8 m length of 0.25 mm diameter copper wire, if wound to give 59 turns, will result in a pickup coil 28' with a 35 mm overall diameter (therefore r=17.5 mm), assuming a 3 mm core diameter.

The remainder of the components depicted in FIG. 2 are components that were not present in the embodiment of device 20 depicted in FIG. 1. The fulcrum frame 42 made of acrylic plastic functions to mount the device 20' within the bore tube of the MRI machine. The fulcrum frame 42 is clamped inside the bore with three Teflon™ screws 44. Within the fulcrum frame 42 are two guide rods 46. Guide rods 46 support the fulcrum housing 48 which holds the fulcrum 24' and allows it to function. In this embodiment, both guide rods 46 and fulcrum housing 48 are made of acrylic plastic. The height adjustment screw 50 functions to clamp fulcrum housing 48 to the guide rods 46 and allows the device 20' to be adjusted to the height of subject 32 and the inner diameter of the RF and gradient coils. It also allows adjustment of the nominal fulcrum angle θ.

The location of the pickup coil 28' on the lever 22' can be adjusted by the coil-fulcrum distance adjustment screw 54 that is made of nylon in this embodiment. The coil mounting 38' allows adjustment of coil angle α.

The stationary rod 56 is designed to support output terminal block 58. Stationary rod 56 is made of a ¼ inch (0.62 cm) wooden dowel (about 2 ft, or 61 cm in length) in this embodiment. Output terminal block 58 in this embodiment is a double binding post assembly(commercially available as part no. 4243-0, Pomona Electronics, Pomona Calif.). Output terminal block 58 allows connection of signal transmittal means 62 for data collection from the device 20'. Signal transmittal means 62 functions to transmit the signal produced in the device 20' to the processor, or MRI machine. Signal transmittal means 62 can comprise anything that can function to transmit an electrical signal, examples include but are not limited to, flexible wires that allow lever 22' to move freely, a commutator and brushes, or an optical coupler. The safety clamp 60 functions to lock lever 22' in place when not in use to minimize the risk of damaging the device 20' by affecting signal transmittal means 62. Safety clamp 60 includes a nylon clamp that attaches to lever 22'.

FIG. 2 and the description thereof offered above are meant to be an illustrative example of a device in accordance with one aspect of the invention. This device 20' was constructed for use with a Bruker 1.9 T/31 cm Biospec MRI scanner equipped with 20 cm inner diameter shielded gradients and a 15 cm inner diameter birdcage proton resonator by Bruker Medizintechnik GmbH, Ettlingen, Germany.

Such a device could be configured with different dimensions to be used in other MRI machines. Examples of such machines include but are not limited to, GE Signa scanners (GE Medical Systems, Waukesha, Wis.); Hitachi MRI scanners (Hitachi Medical Systems, Twinsburg, Ohio), Marconi MRI scanners (Marconi Medical Systems, Cleveland, Ohio), Phillips MRI scanners (Phillips Medical Systems, Best, Netherlands), Siemens Magnetom machines (Siemens Medical Systems, Erlangen, Germany); Toshiba MRI scanners (Toshiba Medical Systems, Tustin, Calif.); and Varian MRI machines (Varian, Palo Alto, Calif.).

Generally, the MRI machines that are listed above are used for clinical MRI of human subjects. Typically, such machines have dimensions that correspond with the following generalized dimensions. Typically, the diameter of the magnet bore is 1000 mm, the distance from the front or back of the magnet to the center of the magnetic field is about 1000 to 1500 mm, and preferably about 1200 to 1362 mm, and the diameter of the gradient bore is about 680 mm. Typically this creates a sensitive region of the radio frequency resonator that can be defined generally by about a 500 mm sphere centered at the center of the magnetic field. Therefore, D, the distance from the center of the magnet to the pickup coil would be about 500 mm in most general purpose clinical MRI machines.

Generally, in human clinical scans, the subjects are scanned with localized . surface coils or phased-array coils rather than radio frequency resonators, so the relevant inner diameter is that of the gradient tube. The resulting dimensions of a device 20 of the invention given these constructs will also depend in part upon the cross-sectional height of the patient at the position (whether it be abdominal, thoracic, or other), and where the slices are taken (the dimension ("h"). However, given these constructs and the other important factors, a device 20 of the invention, if configured analogously to the device discussed in reference to FIG. 2, would typically have a distance L equal to about the half length of the magnet, i.e. about 1000 to 1362 mm, depending on the specific magnet. This distance of L assumes a nominal fulcrum angle, θ, which is close to zero. Such a configuration of θ is likely because there is generally only a small gap between the subject and the gradient tube in which the lever 22 can move.

Example 2

Throughout Examples 2 through 4, the following experimental parameters were constant. A 400 g Wistar rat was anesthetized by inhalation of 2% isoflurane/oxygen at a flow rate of 1 l/min through a mask. The anesthetized rat was placed in a prone position in a Bruker 1.9 T/31 cm Biospec MRI scanner equipped with 20 cm ID shielded gradients and a 15 cm ID transmit/receive birdcage proton resonator (Bruker Medizintechnik GmbH, Ettlingen, Germany). The temperature within the magnet was approximately 25° C.(temperature was unregulated).

The device was configured so that the lever and counterweight were located inside the resonator. The counterweight with the optional paddle attached was placed upon the animal's back.

Output signals were routed through the Faraday cage filter plate (Lindgren RF Enclosures, Glendale Heights, Ill.), and the signal was digitized and recorded with a PowerLab 4/SP data acquisition system (AD Instruments, Castle Hill, Australia).

Example 2 was designed to examine the dependence of the amplitude of the signal generated from the device on the distance between the center of the $B_0$ field and the center of the pickup coil, D.

Figure 3:
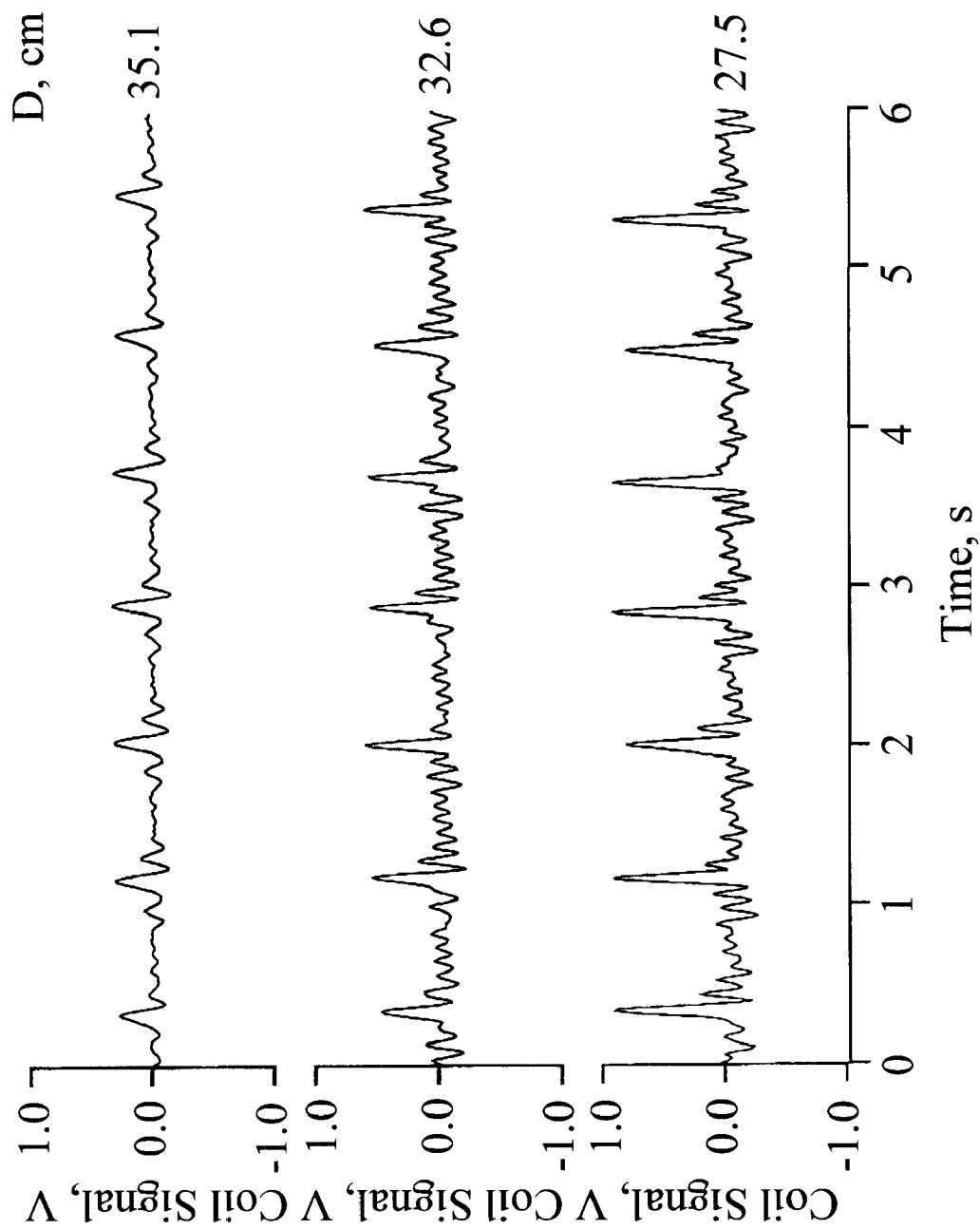
FIG. 3 is a graph of a signal in volts (v) from a device of the invention with a subject to pickup coil distance, D of 27.5, 32.6, and 35.1 cm.

The experimental conditions enumerated above were utilized along with L (the length from the counterweight to the fulcrum) of 12.7 cm, θ=0°, and α=0°. D was varied between 27.5 cm and 35.1 cm. FIG. 3 shows the signals from the device with D=35.1 cm in the top panel, D=32.6 cm in the middle panel and D=27.5 cm in the bottom panel. Table 1 below displays the mean and the standard deviation of the peak-to-peak voltage over six consecutive respiratory cycles.

TABLE 1

| Distance from magnet center to center of pickup coil - D (cm) | Peak to peak voltage of the signal - $V_{pp}$ (volts) and standard deviation (volts) |
|---|---|
| 27.5 | 1.148 ± 0.030 |
| 32.6 | 0.734 ± 0.045 |
| 35.1 | 0.429 ± 0.032 |

The theory of operation of the device predicts that there should be no explicit dependence of the signal on the distance D. The results comply with that theory, because the decrease in signal amplitude with increasing distance D is fairly slow until the coil is almost outside the bore of the magnet. The variation in signal amplitude that is seen is due to the fall-off of the $B_0$ field with increasing distance from the center of the magnet.

The results show that the dependence of the signal on the distance D, coil-magnet distance, is fairly weak. This allows for the coil to be placed quite far away from the center of the magnet with very little loss of signal. Because of the ability to place the coil at a substantial distance from the magnet, coupling between the coil and the resonator and/or gradients can be effectively eliminated while still maintaining a strong signal from the coil.

Example 3

Example 3 was designed to examine the dependence of the amplitude of the signal generated from the device on the nominal fulcrum angle, θ.

Figure 4:
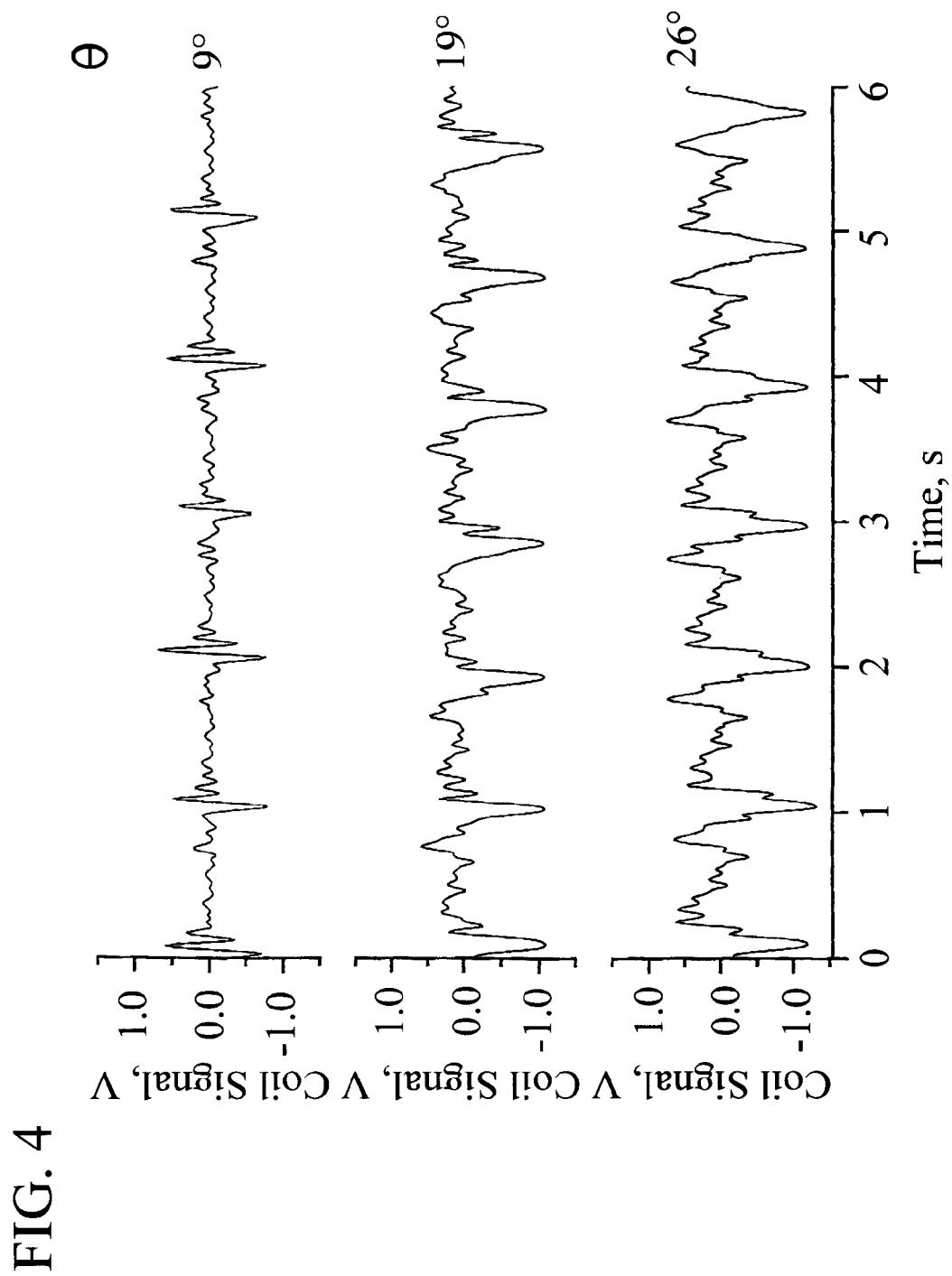
FIG. 4 is a graph of a signal in volts (v) from a device of the invention with a nominal fulcrum angle, $\theta$, of 9°, 19° and 26°.

The experimental conditions enumerated above were utilized along with L=12.7 cm, D=27.5 cm, and α=θ. The nominal fulcrum angle, θ was varied from 9°, the lever nearly horizontal and parallel to the magnetic field, to 26°, the counterweight almost touching the inside of the resonator. FIG. 4 shows the signals recorded from the device with θ=9° in the top panel, θ=19° in the middle panel, and θ=26° in the bottom panel. Table 2 below displays the mean and the standard deviation of the peak-to-peak voltage over five consecutive respiratory cycles.

TABLE 2

| Nominal fulcrum angle - θ (°) | Peak to peak voltage of the signal - $V_{pp}$ (volts) and standard deviation (volts) |
|---|---|
| 9 | 1.317 ± 0.097 |
| 19 | 1.564 ± 0.089 |
| 26 | 1.935 ± 0.085 |

The theory of operation of the device predicts that the signal amplitude should be proportional to 1/cos θ when, as here, θ=α. This assertion is based upon the following equation:

$$\text{For } \alpha = \theta \qquad \varepsilon = \frac{B\pi r^2}{L\cos\theta}\frac{dh}{dt}$$

Therefore, a weak dependence on θ should be seen until θ becomes considerably larger than 26°. The results given above comply with that theory, as the nominal angle between the magnet axis and the lever, θ increases, the amplitude of the signal generated by the pickup coil increases. The dependence of coil signal amplitude on θ is rather weak though, as predicted, with the small available range of θ within the MRI magnet bore.

Example 4

Example 4 was designed to examine the dependence of the amplitude of the signal generated from the device on the coil angle, α.

Figure 5:
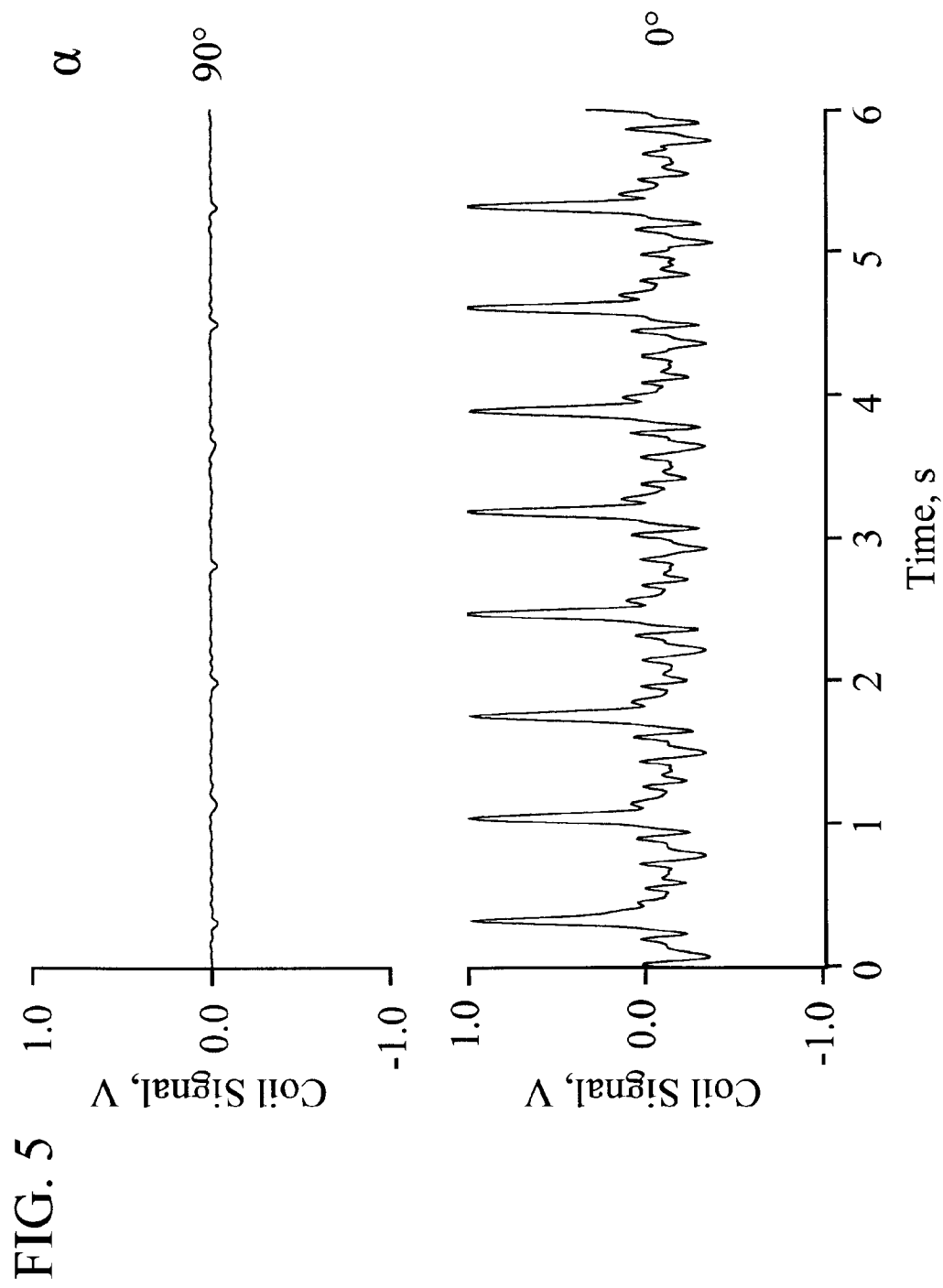
FIG. 5 is a graph of a signal in volts (v) from a device of the invention with a pickup coil angle, $\alpha$, of 0 and +90°.

The experimental conditions enumerated above were utilized along with L=12.7 cm, D=27.5 cm, and θ=0°. The coil angle, α was changed from α=θ, the plane of the pickup coil parallel to $B_0$, to α=θ+90°, the plane of the pickup coil perpendicular to $B_0$. FIG. 5 shows the two signals generated from the device with α=θ+90° in the top panel and α=θ°0° in the bottom panel.

The theory of operation of the device predicts a maximum signal for α=θ, i.e. the pickup coil parallel to $B_0$. By comparing the two graphs depicted in FIG. 5, the top at α=θ+90°, and the bottom at α=θ, it can be seen that the signal is much stronger at α=θ, as the theory would predict.

It was also determined that the dependence on α–θ is weak for small values of α=θ. Therefore, the coil angle α is not critical as long as the plane of the coil is reasonably close to parallel with the magnetic field.

The results of Example 4 showed high-frequency oscillations visible near the baseline of the graphs. It was determined that these oscillations were not due to electronic noise, because the amplitude of the oscillations decreased as the overall signal decreased when α=θ+90° compared to when α=θ=0°, while the electronics of the system did not change. Therefore, it was determined that the oscillations must arise from some rapid motion of the lever between breaths.

Figure 6:
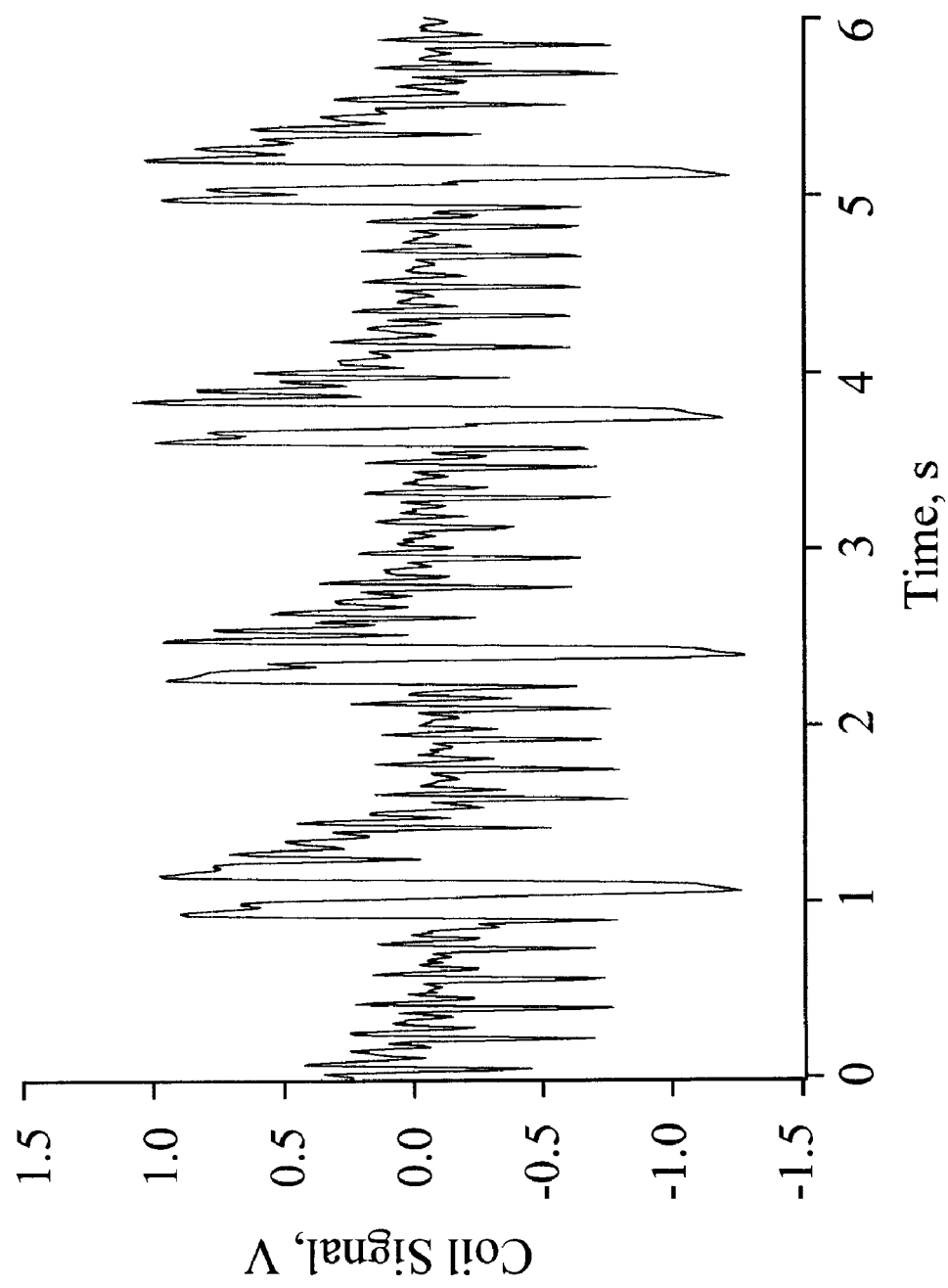
FIG. 6 is a graph of a signal in volts (v) from a device of the invention showing the sharp high frequency peaks in between respiratory peaks.

It was shown that by moving the counterweight to a different location on the animal's back, it was possible to resolve the high frequency oscillations between breaths into a sequence of sharp, regularly spaced peaks, FIG. 6. Upon further examination, it was found that the average period of the respiratory peaks was 1.33 seconds, which corresponds to a respiratory rate of 45/minute, and the average period of the smaller high frequency oscillations was 0.17 seconds, which corresponds to a rate of 353/minute, which is consistent with the heart rate of a lightly anesthetized rat.

Example 5

Example 5 was designed to more fully examine the high frequency device signal and the cardiac motion of the subject.

The experimental parameters for Example 5 are as follows. A 20 g male C57B1 mouse was anesthetized by inhalation of 2% isoflurane/oxygen at a flow rate of 1 l/min through a mask. The anesthetized mouse was placed in a prone position in a Bruker 1.9 T/31 cm n Biospec MRI scanner equipped with 20 cm ID shielded gradients and a homemade saddle coil (Bruker Medizintechnik GmbH Ettlingen, Germany). The temperature within the magnet was approximately 25° C.(temperature was unregulated);

The device was configured so that only the counterweight was located inside the resonator. The device was configured with L=12.7 cm, D=27.5 cm, θ=19° and α=θ. The counterweight was placed on the animal's back.

In this example, the counterweight used earlier was replaced with a smaller counterweight. A 10–32 (outer diameter of 0.19 inches (0.48 cm) and 1 inch (2.54 cm long) Teflon™ screw was fastened on the end of the lever to modify the counterweight. The counterweight tip of the device was inserted into a hole drilled through the housing of a homemade 35 mm diameter saddle coil surrounding the mouse's body. All parts of the device except the counterweight were placed outside the coil (this allowed the device to be used in the smaller diameter of the mouse imaging RF coil). Carbon fiber ECG leads (Vitaline, Yarmouth Port, Mass.), terminated by graphite pads coated with conductive paste were attached to three of the animal's paw using plastic paper clips.

Output signals were routed through the Faraday cage filter plate (Lindgren RF Enclosures, Glendale Heights, Ill.). The ECG leads were attached to filters in the walls of the Faraday cage. The signal from the device and the ECG were digitized and recorded with a PowerLab 4/SP data acquisition system (AD Instruments, Castle Hill, Australia).

Figure 7:
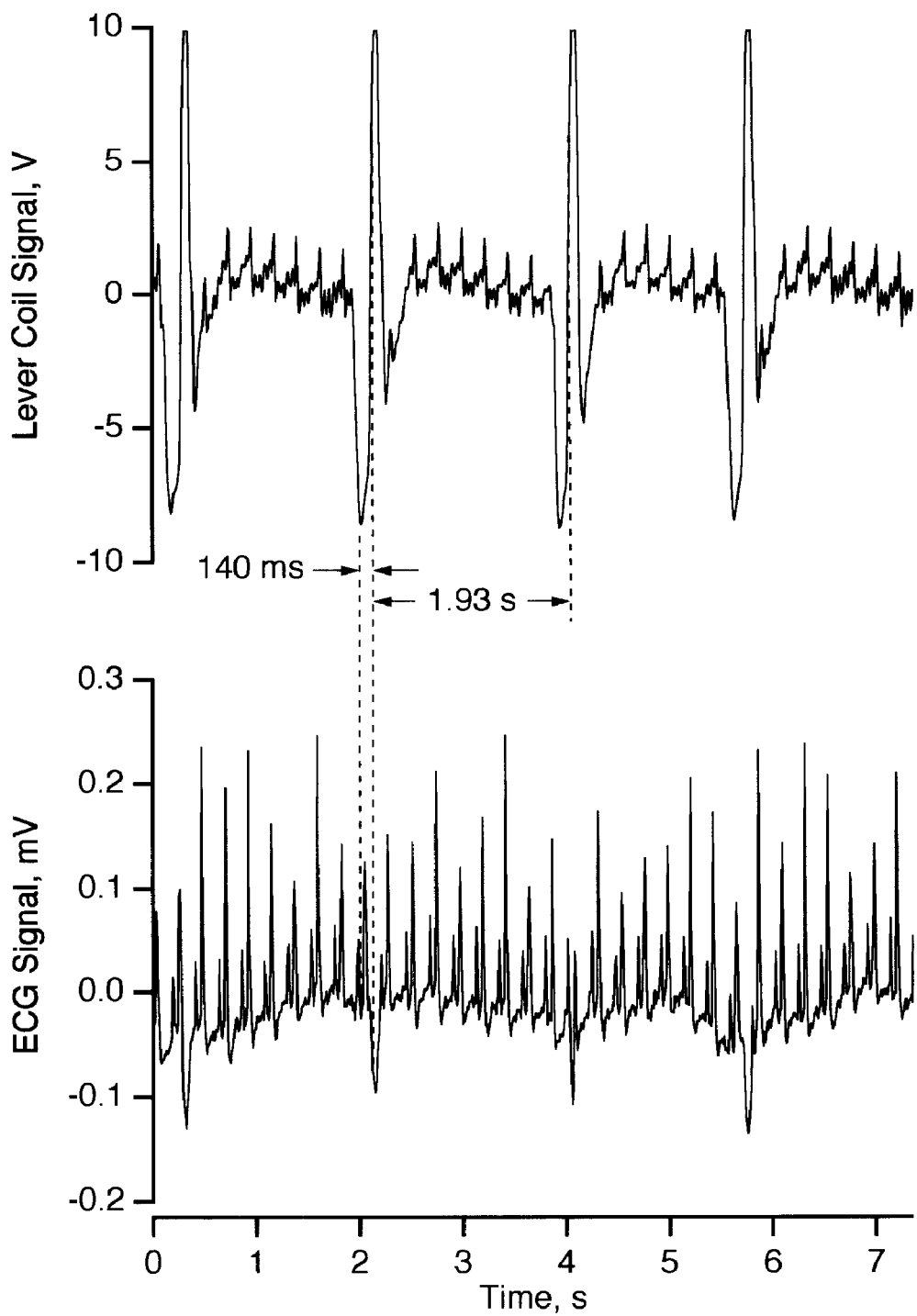
FIG. 7, top panel, is a graph of a signal, in volts (v), from a device of the invention and bottom panel, is a graph of an electrocardiogram signal, in millivolts.

FIG. 7 illustrates the device signal and the simultaneous ECG trace for the mouse anesthetized with isoflurane. As would be expected, under these anesthetic conditions, the mouse exhibited characteristic "snap breathing" behavior, which is evidenced by the large, sharp peaks in the device signal (top panel of FIG. 7). Consistent respiratory artifact peaks can be seen in the ECG signals that coincide closely with the zero crossing of each lever coil signal.

Figure 8:
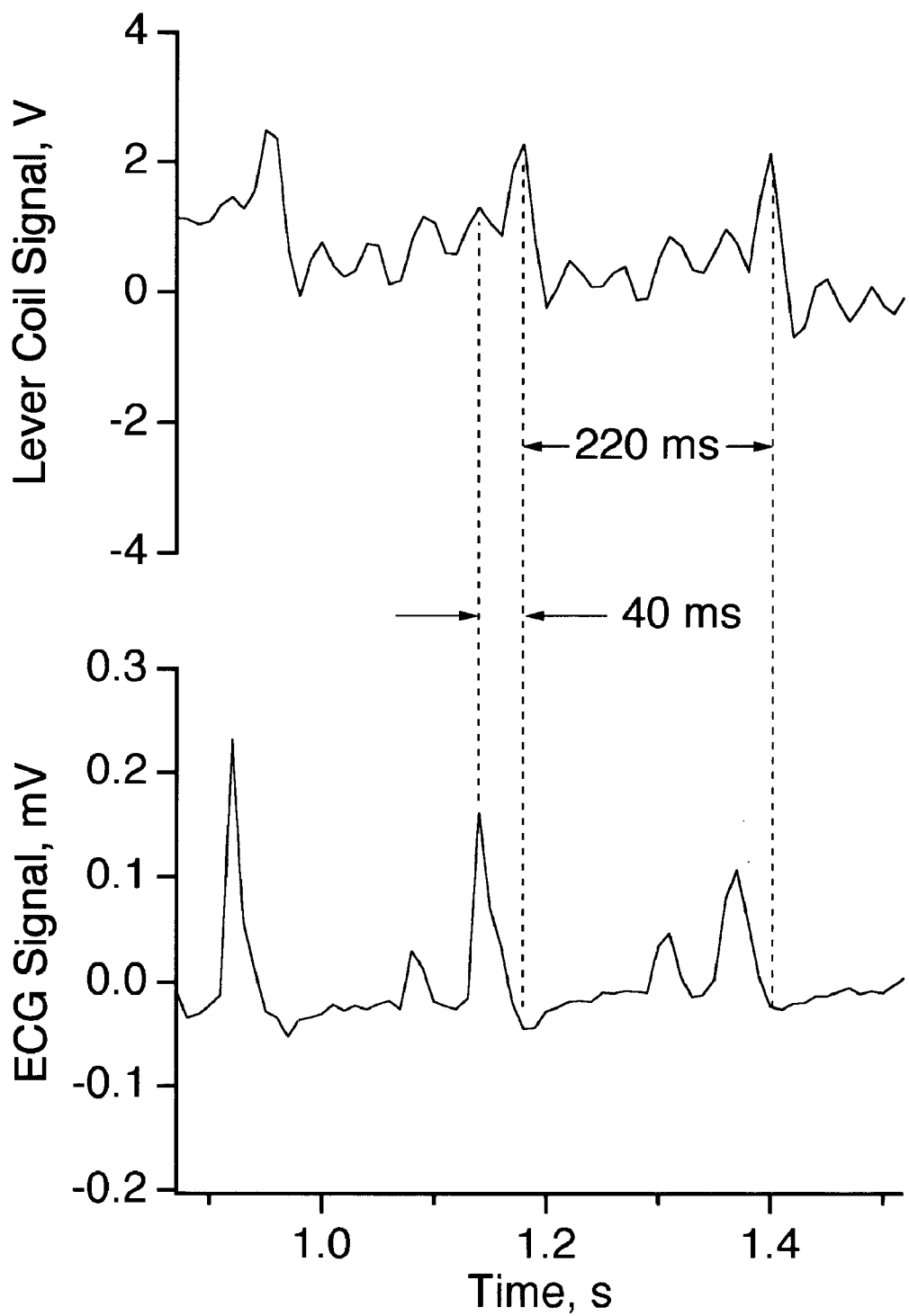
FIG. 8, depicts magnified regions of the graphs shown in FIG. 7.
Figure 9:
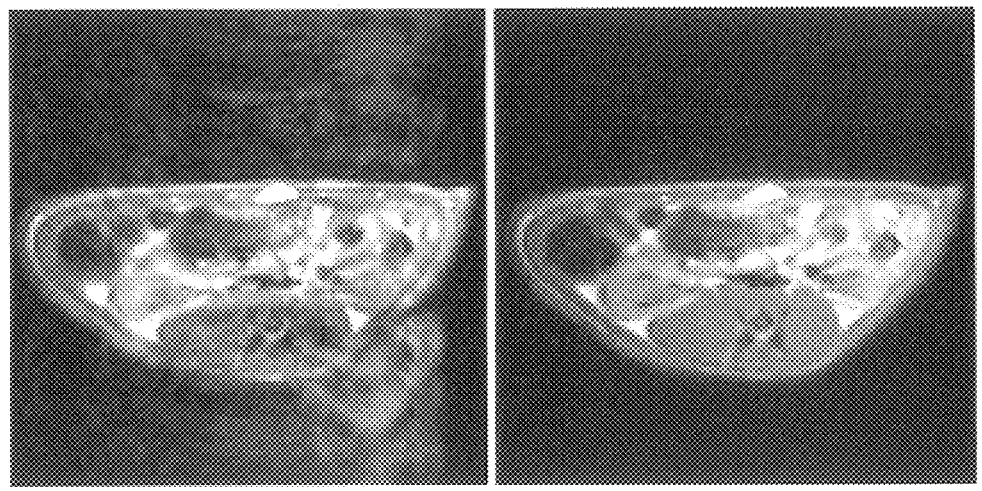
FIG. 9, left panel is a MRI image of the abdomen of a rat acquired using a device of the invention, and right panel is a MRI image of the abdomen of a rat acquired without a device of the invention.

FIG. 8, which is a portion of FIG. 7 in greater detail, shows a consistent delay of 30 to 40 milliseconds between each ECG R wave and the subsequent peak in the device signal. The period of the high frequency device oscillations (220–230 milliseconds), which corresponds to a rate of 273–261/minute, and their temporal relation to the ECG R waves demonstrate that these oscillations are associated with cardiac motion in the mouse.

Example 6

Example 6 was designed to demonstrate the use of the device in an abdominal MRI experiment using respiratory gating.

The experimental parameters for Example 6 are as follows. A 400 g Wistar rat was anesthetized by inhalation of 2% isoflurane/oxygen at a flow rate of 1 l/min through a mask. The anesthetized rat was placed in a prone position in a Bruker 1.9 T/31 cm Biospec MRI scanner equipped with 20 cm ID shielded gradients and a 15 cm ID birdcage proton resonator (Bruker Medizintechnik GmbH, Ettlingen, Germany). The temperature within the magnet was approximately 25° C.(temperature was unregulated).

The device was configured so that the lever and counterweight were located inside the resonator. The device was configured with L=12.7 cm, D=27.5 cm, $\theta$=0°, and $\alpha$=$\theta$. The counterweight was placed upon the animal's back.

Output signals were routed through the Faraday cage filter plate (Lindgren RF Enclosures, Glendale Heights, Ill.), and the signal was digitized and recorded with a PowerLab 4/SP data acquisition system (AD Instruments, Castle Hill, Australia).

Imaging parameters were TE (echo time)=15 ms, FOV (field of view)=20×20 cm, NEX (number of averages)=2, slice thickness=2 mm, matrix size=256×256, and total scan time was approximately 10 minutes per image.

In the respiratory-gated experiment, data acquisition was triggered 500 milliseconds after each negative-going respiratory peak in the device signal. Because the device signal is proportional to dh/dt, this is equivalent to triggering data acquisition on the slope of the respiratory waveform with an added delay. With an average respiratory rate of 50/minute, this resulted in an average TR of 1.2 seconds, and caused data acquisition to take place at a time when respiratory motion was essentially absent. Trigger signals were generated by a simple threshold detector and a one-shot multivibrator (Coulbom Instruments, Allentown, Pa.).

Figure 10:
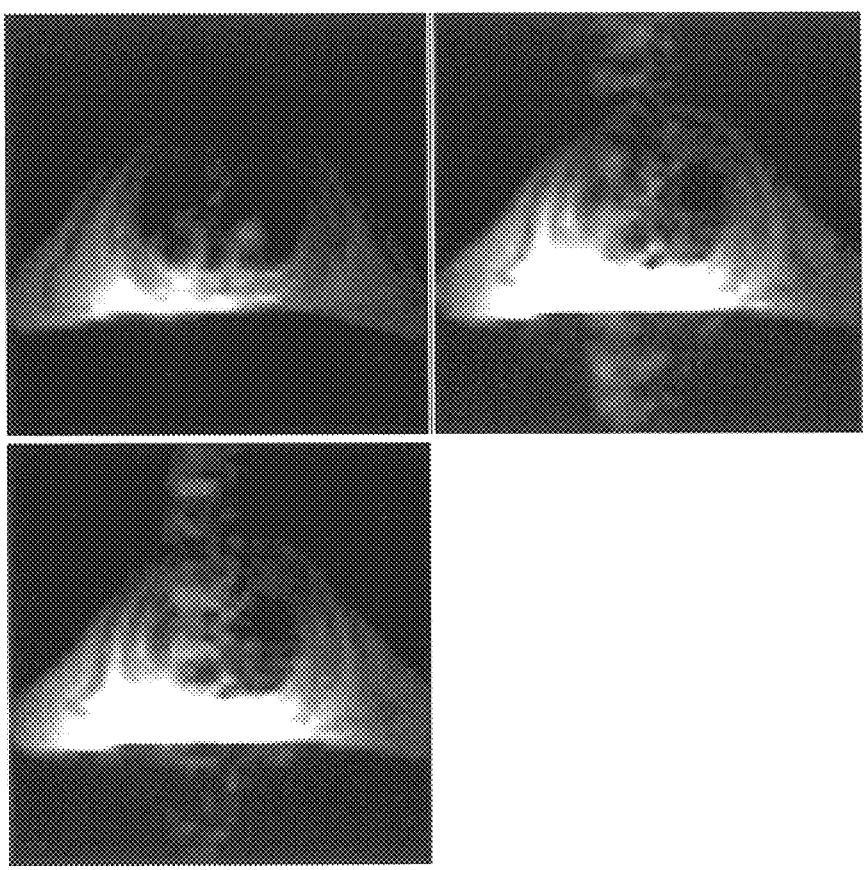
FIG. 10, top left panel is a MRI image of the heart and thorax of a rat acquired using cardiorespiratory gating synchronized to a signal from a device of the invention; the top right panel of this figure is a MRI image of the heart and thorax of a rat acquired using only respiratory gating synchronized to a signal from a device of the invention; the bottom left panel of this figure is a MRI image of the heart and thorax of a rat acquired with neither respiratory nor cardiac gating.

The abdominal images in FIG. 10 were acquired with the respiratory gating parameters described above (left panel of FIG. 10) and with no respiratory gating and a fixed TR of 1.2 seconds (right panel of FIG. 10). The abdominal image without gating shows severe blurring along the phase encoded (vertical) direction as well as in-plane artifacts. Use of the device for respiratory gating substantially eliminates respiratory motion artifacts along the phase-encoded direction. Also, the absence of artifacts and the clean image of the upper abdomen, demonstrate that the presence of the lever coil in the magnet bore neither results in visible RF interference effects from the coil leads nor causes any degradation of image quality due to mutual inductance between the RF and pickup coils.

Example 7

Example 7 was designed to illustrate the use of the device in a MRI experiment using both respiratory and cardiac gating.

The experimental parameters for Example 7 are as follows. A 400 g Sprague-Dawley rat was anesthetized by inhalation of 2% isoflurane/oxygen at a flow rate of 1.2 l/min through a mask. The anesthetized rat was placed in a prone position in a Bruker 1.9 T/31 cm Biospec MRI scanner equipped with 20 cm ID shielded gradients, a 15 cm ID transmit-only birdcage proton resonator, and a 30 mm receive-only surface coil placed under the rat's heart. The rectal temperature of the rat was monitored and maintained at 37° C. by means of a stream of warm air blowing through the magnet bore. The pulse rate and blood oxygen saturation of the rat were monitored throughout the experiment using a veterinary pulse oximeter (Model 8600V, Nonin Medical, Plymouth, Minn.) with a clip sensor attached to one hind paw. The animal's blood oxygen saturation ($SpO_2$) was between 98 and 100% at all times. Under these anesthetic conditions, the rat's average respiratory and cardiac cycle times were 1.1 s and 160 ms, respectively.

The device was configured so that the lever and counterweight were located inside the resonator. The device was configured with L=12.7 cm, D=27.5 cm, $\theta$=0° and $\alpha$=$\theta$. The counterweight used was identical to that used in example 5 except that Teflon nuts were threaded onto the screw tip to damp lever oscillations following each breath. This counterweight was applied to the animal's back, above and to the right of the heart as viewed from behind the rat's head.

Output signals were routed through the Faraday cage filter plate (Lindgren RF Enclosures, Glendale Heights, Ill.), and the signal was digitized and recorded with a PowerLab 4/SP data acquisition system (AD Instruments, Castle Hill, Australia). To generate the required trigger signals, the signal from the device was connected to a Tektronix 2465B oscilloscope (Tektronix, Beaverton, Oreg.). The "A" trigger level was set so that each positive-going respiratory peak from the device would start the "A" sweep and generate a TTL logic pulse at the oscilloscope's "A" gate output. This logic pulse was used to trigger MRI signal acquisition in the respiratory-gated experiment. Following the beginning of each "A" sweep, a delay of 200 ms was executed by the oscilloscope, followed by the detection of a "B" trigger event. The "B" trigger level was set so that a positive-going cardiac peak from the device would start the "B" sweep. In this manner, the "B" sweep began with the first cardiac peak detected at least 200 ms after each respiratory peak. At the beginning of each "B" sweep, the oscilloscope generated a TTL logic pulse at its "B" gate output and this signal was used to trigger MRI acquisition for the cardiorespiratory-gated experiment. The "A" and "B" trigger polarity and level were set by observing the cardiorespiratory waveform from the device on the oscilloscope display screen.

Imaging parameters were $TR_{min}$ (minimum repetition time)=2 s, TE (echo time)=9.5 ms, FOV (field of view)= 10×10 cm, NEX (number of averages)=2, slice thickness=2 mm, acquisition time=2.56 ms, matrix size=64×64, and total scan time was approximately 4.7 minutes per experiment. The imaging slice was taken in the transverse direction, passing obliquely through the right and left ventricles of the rat's heart.

Figure 11:
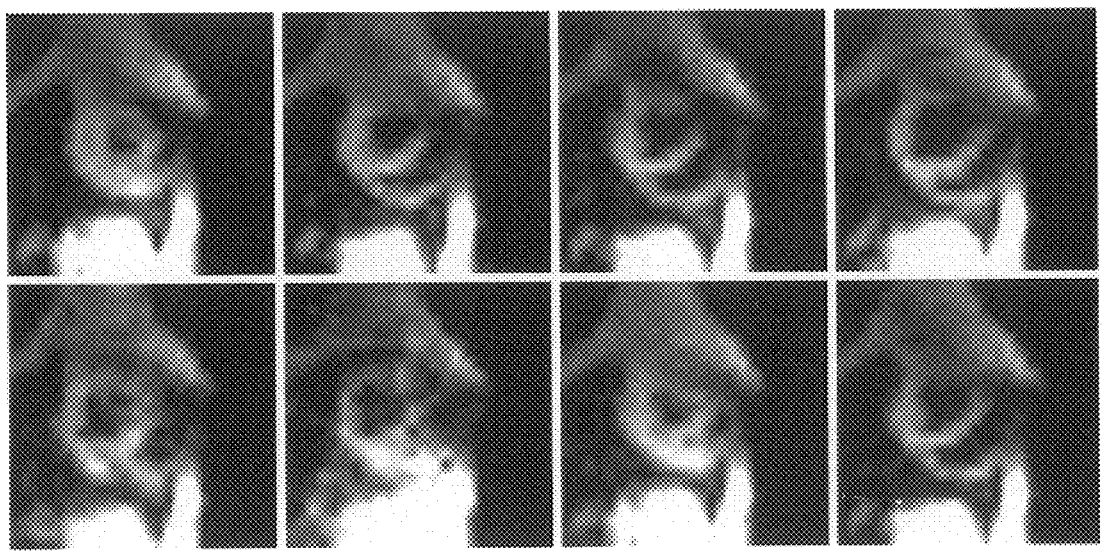
FIG. 11 is a sequence of MRI images of a mouse's heart at various stages of the cardiac cycle acquired with cardiorespiratory synchronization to a signal from a device of the invention.

Three separate experiments were performed using this setup. First an image was acquired with a fixed repetition time of 2.2 s with neither respiratory nor cardiac gating. As expected, this image (FIG. 11, bottom left panel) shows severe artifacts along the phase-encoded (vertical) direction, totally obscuring the anatomy of the heart. In a second experiment, the acquisition of each phase-encoded step was triggered 251 ms after a positive-going respiratory peak in the lever-coil signal while maintaining a minimum repetition time of 2 seconds. Although acquisition took place only during end-expiration, while the rat's chest was relatively stationary, the resulting image (FIG. 11, top right panel) still shows severe blurring due to the lack of synchronization of the MRI acquisition with both the respiratory and cardiac cycles of the subject. Finally, an experiment was performed with both respiratory and cardiac gating. In this experiment, the acquisition of each phase-encoded step was initiated 1 ms after the first positive-going cardiac peak occurring at least 200 ms after a positive-going respiratory peak. Again, a minimum repetition time of 2 s was maintained throughout the experiment, regardless of the actual respiratory cycle time. These timings ensured that acquisition would take place not only during end-expiration but also at a constant phase in the cardiac cycle. The cardiorespiratory-gated image thus obtained (FIG. 11, top left panel) is free of motion-induced blurring and permits identification of the right and left ventricle walls at early systole. Thus, the capability of the device to detect respiratory and cardiac motion with sufficient accuracy and reliability to yield cardiorespiratory-gated images of the rat heart free from motional blurring was demonstrated.

Example 8

Example 8 was designed to illustrate the use of the device in a MRI experiment using both respiratory and cardiac gating to yield blur-free images of a mouse heart at various phases of the cardiac cycle.

The experimental parameters for Example 8 are as follows. A 20 g C57BL mouse was anesthetized by inhalation of 1.5% isoflurane/oxygen at a flow rate of 1.0 l/min through a mask. The anesthetized mouse was placed in a prone position in a Bruker 1.9 T/31 cm Biospec MRI scanner equipped with 20 cm ID shielded gradients, a 15 cm ID transmit-only birdcage proton resonator, and a 30 mm receive-only surface coil placed under the mouse's heart. The core temperature of the mouse was maintained by means of a stream of 37° C. air blowing through the magnet bore. Under these anesthetic conditions, the mouse's average respiratory and cardiac cycle times were 2.4 s and 180 ms, respectively.

The device was configured so that the lever and counterweight were located inside the resonator. The device was configured with L=12.7 cm, D=27.5 cm, $\theta$=19° and $\alpha$=$\theta$. The counterweight used was identical to that used in example 5 except that Teflon nuts were threaded onto the screw tip to damp lever oscillations following each breath. This counterweight was applied to the animal's back.

Output signals were routed through the Faraday cage filter plate (Lindgren RF Enclosures, Glendale Heights, Ill.), and the signal was digitized and recorded with a PowerLab 4/SP data acquisition system (AD Instruments, Castle Hill, Australia). To generate the required trigger signals, the signal from the device was connected to a Tektronix 2465B oscilloscope (Tektronix, Beaverton, Oreg.). The "A" trigger level was set so that each positive-going respiratory peak from the device would start the "A" sweep. Following the beginning of each "A" sweep, a delay of 750 ms was executed by the oscilloscope, followed by the detection of a "B" trigger event. The "B" trigger level was set so that a positive-going cardiac peak from the device would start the "B" sweep. In this manner, the "B" sweep began with the first cardiac peak detected at least 750 ms after, each respiratory peak. At the beginning of each "B" sweep the oscilloscope generated a TTL logic pulse at its "B" gate output and this signal was used to trigger MRI acquisition for each experiment. The "A" and "B" trigger polarity and level were set by observing the signal from the device on the oscilloscope display screen.

Imaging parameters were $TR_{min}$ (minimum repetition time)=2 s, TE (echo, time)=12.4 ms, FOV (field of view)= 5×5 cm, NEX (number of averages)=1, slice thickness=1 mm, acquisition time=1.28 ms, matrix size=64×64, and total scan time was approximately 2.6 minutes per experiment. The imaging slice was taken along the short axis of the heart, as detected by an initial coronal pilot scan.

In this experiment, the acquisition of each phase-encoded step was initiated a constant time after the first positive-going cardiac peak occurring at least 750 ms after a positive-going respiratory peak. A minimum repetition time of 2 s was maintained throughout the experiment, regardless of the actual respiratory cycle time. These timings ensured that acquisition would take place not only during end-expiration but also at a constant phase in the cardiac cycle. Eight separate experiments were performed in which the delay between the cardiorespiratory trigger signal obtained from the device's output signal and the beginning of MRI acquisition took on values of 1 ms, 25 ms, 50 ms, 75 ms, 100 ms, 125 ms, 150 ms, and 200 ms. The resulting images (FIG. 12, top left to bottom right) clearly show the progression of the mouse heart through the cardiac cycle. In particular, the image acquired with a 1 ms delay (FIG. 12, top left) shows right and left ventricle dimensions consistent with the 40 ms propagation delay observed in Example 5 between each ECG R wave and the subsequent cardiac peak in the device's output signal. Successive images show changes in the ventricle dimensions as the heart passes through diastole and then into systole again. Thus, the capability of the device to detect respiratory and cardiac motion with sufficient accuracy and reliability to yield a timed sequence of cardiorespiratory-gated images of the beating mouse heart was demonstrated.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A device for detection of mammalian cardiac motion, respiratory motion or combinations thereof, during acquisition of a magnetic resonance image comprising:
    (a) a lever having a proximal and a distal end;
    (b) a counterweight on said proximal end of said lever;
    (c) a fulcrum;
    (d) a pickup coil attached to said distal end of said lever; and
    (e) a magnetic resonance imaging machine comprising a radio frequency resonator, a gradient coil, and a magnet that produces a magnetic field comprising a magnet z axis, said pickup coil is positioned outside the sensitive region of said radio frequency resonator; and
    wherein said lever, said fulcrum, said counterweight, and said pickup coil are configured so that said lever action occurs relative to the magnet z axis.

2. The device of claim 1, wherein said pickup coil is positioned outside said radio frequency resonator coil and close enough to the center of said magnetic field to generate an electrical signal in said device through electromagnetic induction.

3. The device of claim 2, wherein said electrical signal can be used to detect and monitor said respiratory motion, cardiac motion, or combination thereof.

4. The device of claim 1, wherein said pickup coil is at least about 500 mm from the center of the magnet.

5. The device of claim 1, wherein said sensitive region of said radio frequency resonator coil corresponds generally with a region in said magnetic resonance imaging machine where nuclear spins can be detected if they are present in that area.

6. The device of claim 1, wherein said sensitive region of said radio frequency resonator coil corresponds generally with the homogeneous region of said magnetic field.

7. The device of claim 1, wherein said fulcrum is positioned outside said radio frequency resonator and said gradient coil.

8. The device of claim 1, wherein said counterweight is positioned within said magnetic field and in contact with said subject.

9. A device for respiratory gating of a magnetic resonance imaging experiment comprising:
    (a) a lever having a proximal and a distal end;
    (b) a counterweight on said proximal end of said lever;
    (c) a fulcrum;
    (d) a pickup coil attached to said distal end of said lever;
    (e) a threshold detector wherein said threshold detector is used to trigger acquisition of the individual scans of the magnetic resonance image; and
    (f) a magnetic resonance imaging machine comprising a radio frequency resonator, a gradient coil, and a magnet that produces a magnetic field comprising a magnet z axis and wherein said pickup coil is positioned outside the sensitive region of said radio frequency resonator.

10. The device of claim 9, wherein said pickup coil is positioned outside said radio frequency resonator coil and close enough to the center of said magnetic field to generate an electrical signal in said device through electromagnetic induction.

11. The device of claim 10, wherein said electrical signal can be used to detect and monitor said respiratory motion, cardiac motion, or combination thereof and said threshold detector can be used to trigger acquisition of said magnetic resonance image.

12. The device of claim 9, wherein said sensitive region of said radio frequency resonator coil corresponds generally with a region in said magnetic resonance imaging machine where nuclear spins can be detected if they are present in that area.

13. The device of claim 9, wherein said sensitive region of said radio frequency resonator coil corresponds generally with the homogeneous region of said magnetic field.

14. The device of claim 9, wherein said pickup coil is at least about 500 mm from the center of the magnet.

15. The device of claim 9, wherein said fulcrum is positioned outside said radio frequency resonator and said gradient coil.

16. The device of claim 9, wherein said counterweight is positioned within said magnetic field and in contact with said subject.

17. A method of monitoring mammalian cardiac motion, respiratory motion, or combinations thereof, during acquisition of a magnetic resonance image comprising the steps of:
    (a) configuring a device comprising
        (i) a lever having a proximal and a distal end;
        (ii) a counterweight on said proximal end of said lever;
        (iii) a fulcrum;
        (iv) a pickup coil attached to said distal end of said lever; and
        (v) a magnetic resonance imaging machine comprising a radio frequency resonator, a gradient coil, and a magnet that produces a magnetic field comprising a magnet z axis and wherein said pickup coil is positioned outside the sensitive region of said radio frequency resonator; and
        wherein said lever, said fulcrum, said counterweight, and said pickup coil are configured so that said lever action occurs relative to the magnet z axis;
    (b) scanning the subject with said magnetic resonance imaging machine; and
    (b) monitoring the electrical signal produced by said device.

18. The method of claim 17, wherein said device further comprises a threshold detector.

19. The method of claim 18, further comprising the step of triggering said scanning of said magnetic resonance imaging machine using said threshold detector, wherein said triggering is based on said electrical signal produced by said device.

20. The method of claim 19, wherein said scanning is triggered to commence when there is minimum cardiac motion, respiratory motion, or a combination thereof.

21. The method of claim 17, wherein said device is configured in such a way that said pickup coil is positioned outside said radio frequency resonator coil and close enough to the center of said magnetic field to generate an electrical signal in said device through electromagnetic induction.

22. The method of claim 17, wherein said device is configured so that said pickup coil is at least about 500 mm from the center of the magnet.

23. The method of claim 17, wherein said sensitive region of said radio frequency resonator coil corresponds generally with a region in said magnetic resonance imaging machine where nuclear spins can be detected if they are present in that area.

24. The method of claim 17, wherein said sensitive region of said radio frequency resonator coil corresponds generally with the homogeneous region of said magnetic field.

* * * * *